US011844809B2

(12) United States Patent
Totary-Jain

(10) Patent No.: US 11,844,809 B2
(45) Date of Patent: Dec. 19, 2023

(54) STRATEGY TO INCREASE ANTI-VIRAL, ANTI-MICROBIAL, AND ANTI-FUNGAL DEFENSE

(71) Applicant: University of South Florida, Tampa, FL (US)

(72) Inventor: Hana Totary-Jain, Wesley Chapel, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 72 days.

(21) Appl. No.: 17/834,611

(22) Filed: Jun. 7, 2022

(65) Prior Publication Data

US 2022/0296630 A1  Sep. 22, 2022

Related U.S. Application Data

(62) Division of application No. 16/408,518, filed on May 10, 2019, now Pat. No. 11,357,789.

(60) Provisional application No. 62/669,747, filed on May 10, 2018.

(51) Int. Cl.
| | |
|---|---|
| C07H 21/02 | (2006.01) |
| A61K 31/7105 | (2006.01) |
| A61P 37/04 | (2006.01) |
| A61P 31/04 | (2006.01) |
| A61P 31/12 | (2006.01) |
| A61K 39/12 | (2006.01) |
| A61P 31/10 | (2006.01) |
| C12N 15/11 | (2006.01) |
| A61K 39/00 | (2006.01) |

(52) U.S. Cl.
CPC .......... *A61K 31/7105* (2013.01); *A61K 39/12* (2013.01); *A61P 31/04* (2018.01); *A61P 31/10* (2018.01); *A61P 31/12* (2018.01); *A61P 37/04* (2018.01); *C12N 15/111* (2013.01); *A61K 2039/53* (2013.01); *C12N 2320/30* (2013.01)

(58) Field of Classification Search
CPC ........................... C12N 15/111; C12N 15/113
See application file for complete search history.

(56) References Cited

FOREIGN PATENT DOCUMENTS

CA     2795906 A1    10/2010

OTHER PUBLICATIONS

Amador-Molina et al., "Role of innate immunity against human papillomavirus (HPV) infections and effect of adjuvants in promoting specific immune response" Viruses . Oct. 28, 2013;5(11):2624-42.
Ander et al., Immune Responses at the Maternal-Fetal Interface, Science Immunology, 2019, 4(31), 22 pages.
Andrews et al., "Alu RNA transcribed in vitro binds the 68-kDa subunit of the signal recognition particle" J Biol Chem. Feb. 25, 1987;262(6):2908-12.
Baillie et al., Somatic Retrotransposition Alters the Genetic Landscape of the Human Brain, Nature, 2011, 479 (7374):534-537.
Chang et al., Expression and Trafficking of Placental MicroRNAs at the Feta-Maternal Interface, FASEB Journal, eo11, 31 (7):2160-2110.
Chu et al., Potential Alu Function: Regulation of the Activity of Double-Stranded RNA-Activated Kinase PKR, Molecular and Cellular Biology, 1998, 18(1):58-68.
Churko et al., Generation of Human iPSCs from Human Peripheral Blood Mononuclear Cells Using Non-Integrative Sendai Virus in Chemically Defined Conditions, Methods Mol Biol, 2013, 1036:81-88.
Gombart et al., "Exaptation of an ancient Alu short interspersed element provides a highly conserved vitamin D-mediated innate immune response in humans and primates" BMC Genomics, 2009, 10, 321, 1-11.
Hasler et al., Alu Elements as Regulators of Gene Expression, Nucleic Acids Research, 2006, 34(19):5491-5497.
Hung et al., The Ro60 Autoantigen Binds Endogenous Retroelements and Regulates Inflammatory Gene Expression, Science, 2015, 350(6259):455-459.
Kaneko et al., DICER1 Deficit Induces Alu RNA Toxicity in Age-Related Macular Degeneration, Nature, 2011, 471(7338):325-330.
Kari Ko et al., Incorporation of Pseudouridine into mRNA Yields Superior Nonimmunogenic Vector with Increased Translational Capacity and Biological Stability, Molecular Therapy, 2008, 16(11):1833-1840.
Konermann et al., Genome-Scale Transcriptional Activation by an Engineered CRISPR-Cas9 Complex, Nature, 2015, 517(7536):583-588.
Kotenko et al., IFN-As Mediate Antiviral Protection Through a Distinct Class II Cytokine Receptor Complex, Nature Immunology, 2003, 4(1):69-77.
Lander et al., Initial Sequencing and Analysis of the Human Genome, Nature, 2001, 409:860-921.
Liu et al., Cell Stress and Translational Inhibitors Transiently Increase the Abundance of Mammalian SINE Transcripts, Nucleic Acids Research, 1995, 23(10):1758-1765.
Noguer-Dance et al., The Primate-Specific microRNA Gene Cluster (C19MC) is Imprinted in the Placenta, Human Molecular Genetics, 2010, 19(18):3566-3582.

(Continued)

Primary Examiner — Amy H Bowman
(74) Attorney, Agent, or Firm — QUARLES & BRADY LLP

(57) ABSTRACT

Disclosed herein are compositions and methods for inducing, promoting, or enhancing an immune response in a subject. For example, the disclosed compositions and methods can be used prophylactically to prevent viral/microbial infections or therapeutically to treat acute infections. In some embodiments, the disclosed method involves administering to the subject a composition comprising in vitro transcribed (IVT) RNA comprising short interspersed nuclear elements (SINEs), such as Alu repeats. In some embodiments, the disclosed compositions and methods can be used to induce, promote, or enhance any immune response in a subject, including an anti-viral, anti-microbial, anti-fungal, or anti-parasite response. In some embodiments, the disclosed compositions can be administered to any mucosal barrier, such as lungs or intestines, e.g. to enhance an innate immune response against a virus or pathogen.

11 Claims, 19 Drawing Sheets

(56) References Cited

OTHER PUBLICATIONS

Prqkunina-Olsson et al., A Variant Upstream of IFNL3 (IL28B) Creating a New Interferon Gene IFNL4 is Associated with Impaired Clearance of Hepatitis C Virus, Nature Genetics, 2013, 45(2):164-171.
Roux et al., "Roux et al. (Frontiers in Immunology, 2017, 8, 1038, 1-20)" Frontiers in Immunology, 2017, 8, 1038, 1-20.
Syedbasha et al., Interferon Lambda: Modulating Immunity in Infectious Diseases, Frontiers in Immunology, 2017, vol. 8, Article 119, pp. 1-13.
Uematsu et al., Toll-Like Receptors and Innate Immunity, Journal of Molecular Medicine, 2006, 84(9):712-725.
Wells et al., Type III Interferons in Antiviral Defenses at Barrier Surfaces, Trends in Immunology, 2018, 39(10):848-858.

| Gene Set Name | # Genes in Gene Set (K) | # Genes in Overlap (k) | p-value | FDR q-value |
|---|---|---|---|---|
| Defense response | 1231 | 97 | 3.41E-43 | 1.01E-39 |
| Immune system process | 1984 | 115 | 2.73E-38 | 5.38E-35 |
| Immune response | 1100 | 86 | 5.40E-38 | 7.98E-35 |
| Defense response to virus | 164 | 33 | 3.46E-28 | 2.93E-25 |
| Response to virus | 247 | 38 | 9.67E-28 | 7.16E-25 |
| Innate immune response | 619 | 54 | 2.42E-26 | 1.22E-23 |
| Cytokine mediated signaling pathway | 452 | 47 | 2.48E-26 | 1.22E-23 |
| Response to cytokine | 714 | 57 | 8.34E-26 | 3.53E-23 |
| Response to type I interferon | 68 | 23 | 9.05E-26 | 3.57E-23 |
| Cellular response to cytokine stimulus | 606 | 52 | 4.54E-25 | 1.58E-22 |
| Regulation of immune system process | 1403 | 78 | 9.41E-25 | 3.09E-22 |
| Immune effector process | 486 | 44 | 2.68E-22 | 6.60E-20 |
| Regulation of immune response | 858 | 57 | 6.76E-22 | 1.60E-19 |
| Defense response to other organism | 505 | 43 | 8.61E-21 | 1.76E-18 |
| Inflammatory response | 454 | 37 | 1.94E-17 | 2.94E-15 |
| Regulation of cytokine production | 563 | 39 | 6.17E-16 | 7.60E-14 |

FIG. 1D

STRATEGY TO INCREASE ANTI-VIRAL, ANTI-MICROBIAL, AND ANTI-FUNGAL DEFENSE

CROSS-REFERENCE TO RELATED APPLICATIONS

This application is a divisional application of U.S. patent application Ser. No. 16/408,518, filed May 10, 2019, which claims priority to U.S. Provisional Application No. 62/669,747, filed May 10, 2018, both of which are hereby incorporated herein by reference in their entireties.

BACKGROUND

More than 50% of the human genome is composed of repetitive elements, of which Alu repeats (Alus) are the most abundant and comprise 11% of the genomic sequence. Alus, named after the internal Alu/restriction site found in these repeats, belong to the short interspersed nuclear elements (SINEs) and are evolutionary derived from the 7SL RNA gene. Alus are expressed in germ cells and embryonic pluripotent stem cells but are epigenetically silenced by DNA methylation as the cells differentiate. Alterations of this epigenetic control is implicated in wide range of disorders including autoimmune diseases (Hung, T. et al., Science 350:455-459 (2015)), macular degeneration (Kaneko H. et al., Nature 471:325-330 (2011)), neurologic and neurodegenerative disorders (Baillie, J. K. et al., Nature 479:534-537 (2011)).

Alus contain an internal promoter and can be transcribed independently by RNA polymerase III in response to various stress conditions including viral infection, heat shock, translational inhibition or DNA methyltransferase inhibitors (Liu, W. M. et al., Nucleic Acids Res 23:1758-1765 (1995); Chu, W. M. et al., Mol Cell Biol 18:58-68 (1998)). These independent Alu transcripts are ~300 bp in length and are composed of two monomers separate by an A-rich sequence. Alus can also be embedded within mRNA or long non-coding RNA and transcribed by RNA polymerase II. These embedded Alus are expressed at relatively higher levels and can be full or partial length with one or more copies in the sense or antisense orientation that form intermolecular base-pairing and secondary structures.

Sequencing of the human genome has revealed that Alus are under evolutionary selection as they are distributed non-normally throughout the genome, with the highest Alu density found in chromosome 19 (Lander, E. S. et al., Nature 409:860-921 (2001)). However, the beneficial contribution of Alus to human hosts is still largely unknown.

SUMMARY

Retrotransposons comprise approximately 45% of human genome of which approximately 11% comprise short interspersed elements (SINEs). As disclosed herein, sense and/or antisense SINEs can increase in interferon type III which is known to have antiviral/antimicrobial activity. In addition, sense and/or antisense SINEs can induce innate immune response. Moreover, sense and/or antisense SINEs may form siRNA that target viral, bacterial, fungi and parasite genome for degradation and/or inhibit translation/replication.

Therefore, disclosed herein are compositions and methods for inducing, promoting, or enhancing an immune response in a subject. For example, the disclosed compositions and methods can be used prophylactically to prevent viral/microbial infections. In some embodiments, the disclosed method involves administering to the subject a composition comprising in vitro transcribed (IVT) RNA comprising short interspersed nuclear elements (SINEs). In some embodiments, the disclosed compositions and methods can be used to induce, promote, or enhance any immune response in a subject, including an anti-viral, anti-microbial, anti-fungal, or anti-parasite response. In some embodiments, the disclosed compositions can be administered to any mucosal barrier, such as lungs or intestines, e.g. to enhance an innate immune response against a virus or pathogen.

In some embodiments, the disclosed compositions and methods induce interferon lambda 2 (INFL2), interferon lambda 3 (INFL3), and downstream ISGs. In some embodiments, the disclosed compositions are used in combination with viral antigens to enhance viral immunity.

In some embodiments, the SINE comprises Alu repeats. Alu elements are split into subfamilies, such as AluJ, AluS, and AluY. The dominant S subfamilies included Sx, Sq, Sp and Sc. Ya5 and Yb8 are the dominant Y subfamilies in humans.

Modern Alu elements are about 300 base pairs long and are therefore classified as short interspersed nuclear elements (SINEs). In some embodiments, the composition comprises the full length Alu element. However, fragments of the Alu element can also be used including fragments at least 20, 25, 30, 35, 40, 45, 50, 60, 70, 80, 90, 100, 110, 120, 130, 140, 141, 142, 143, 144, 145, 156, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, or 300 bp in length. The composition can contain sense strands, antisense strands, or a combination thereof. The composition can also comprises combinations of different Alu elements in the same or different orientations.

In some embodiments, the IVT RNA sense strands, antisense strands, or combinations thereof are modified nucleotides to reduce innate immune responses. For example, the IVT RNA strands can comprises modified nucleosides, such as pseudouridine (abbreviated by the Greek letter "psi" or NJ"), N1-methylpseudouridine, 5-methylcytosine (m5C), 5-methyluridine (m5U), 2'-O-methyluridine (Um or m2'-OU), 2-thiouridine (s2U), or N6-methyladenosine (m6A)).

Also disclosed herein is a vaccine composition that contains an in vitro transcribed (IVT) RNA comprising short interspersed nuclear elements (SINEs) as disclosed herein, in a pharmaceutically acceptable carrier. The disclosed vaccine composition can in some embodiments, contain one or more antigens, such as viral antigens. The disclosed vaccine composition can in some embodiments, contain an adjuvant.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A to 1L. Activation of C19MC by induces resident miRNA and cellular defense genes. FIG. 1A. Arrangement of the upstream CpG island, resident miRNA, repetitive elements and the CG content within C19MC. FIGS. 1B and 10. Venn diagrams of upregulated (FIG. 1B) or downregulated miRNAs (FIG. 10) in AdHEK cells transfected with 759-sgRNA/SAM, 620-sgRNA/SAM or GFP transfected Control for 72 hr followed by sRNAseq. Resident miRNA of C19MC are shown in magenta. FIG. 1D. Gene set enrichment analysis performed on differentially expressed mRNAs in 759-sgRNA/SAM and 620-sgRNA/SAM compared to GFP control. FIGS. 1E and 1F. RT-PCR for hsa-miR-517a normalized to U18 (FIG. 1E) or IFNL2/3 normalized to GAPDH (FIG. 1F) in AdHEK cells transfected with 759-sgRNA/SAM or GFP Control for 72 hr. FIGS. 1G and 1H. RT-PCR for the indicated gene normalized to GAPDH in untreated AdHEK293 cells (FIG. 1G) or treated with the indicated amount of IFNL1/3 for 48 hr (FIG. 1H). FIGS. 1I-1L. RT-PCR for hsa-miR-517a normalized to U18 (FIGS. 1I and 1K) or IFNL2/3 normalized to GAPDH (FIGS. 1J and 1L) in the indicated cells transfected with 759-sgRNA/SAM or GFP control. Data represent mean±SEM of a representative experiment of at least three independent experiments performed in triplicate. *$p<0.05$ versus GFP.

FIG. 2A. Representative Immunoblot for DICER1, TUBA1B and GAPDH in HEK293T or NoDICE 2-20 cells (FIGS. 1B and 1C) RT-PCR for miR-517a normalized to U18 (FIG. 2B) or IFNL2/3 normalized to GAPDH (FIG. 2C) in the indicated cells transfected with 759-sgRNA/SAM or BB-sgRNA/SAM for 72 hr. FIG. 2D. IFNL3 protein level in the conditioned media of HEK293T or NoDICE 2-20 cells transfected with 759-sgRNA/SAM or BB-sgRNA/SAM for 72 hr. Data represent the mean±SEM of a representative experiment of at least three independent experiments performed in triplicate. *$p<0.05$ versus BB-sgRNA/SAM.

FIG. 3A. Representative Primer extension to assay for the abundances of Alu RNA in HEK293T and NoDICE 2-20 cells transfected with 759-sgRNA/SAM or BB-sgRNA/SAM for 72 hr. FIG. 3B. Arrangement of the CYP19A1 gene with the repetitive elements and the CG content. FIGS. 3C and 3D. RT-PCT for CYP19A1 normalized to GAPDH (FIG. 3C) and IFNL2/3 normalized to GAPDH (FIG. 3D) in HEK293T cells transfected with 759-sgRNA/SAM (759), 47.2-sgRNA/SAM (47.2), 125.3-sgRNA/SAM (125.3) or BB-sgRNA/SAM (BB) for 72 h. FIGS. 3E-3F. RT-PCR for IFNL2/3 normalized to GAPDH in HEK293T cells (FIG. 3E) or HTR8/SVneo cells (FIG. 3F) transfected for 18 h with dsDNA, in vitro transcribed GFP mRNA or the indicated forward (FIG. 3F) reverse (R) or both RNA fragments. Data represent the mean±SEM of a representative experiment of three independent experiments performed in triplicate. *$p<0.05$ versus BB-sgRNA/SAM (FIGS. 3C and 3D); versus non transfected control cells (NTC, FIGS. 3E and 3F).

FIGS. 4C-4E. In situ hybridization for Alu RNA in human term placenta pretreated with or without RNaseA prior to probing (FIG. 4C); Serial sections of first trimester human placentas stained for Cytokeratin (fetal) and Vimentin (maternal decidual cells) (FIG. 4D); or placental sections of VVT and C19MC-transgenic mice (FIG. 4E). miR-517a/c (purple) Alu RNA (purple) and Nuclei was counterstained in red (FIGS. 4C-4E). Scale bars represent 100 μm in full image and 50 μm in insets; original magnification 10×.

DETAILED DESCRIPTION

Figure 1A:
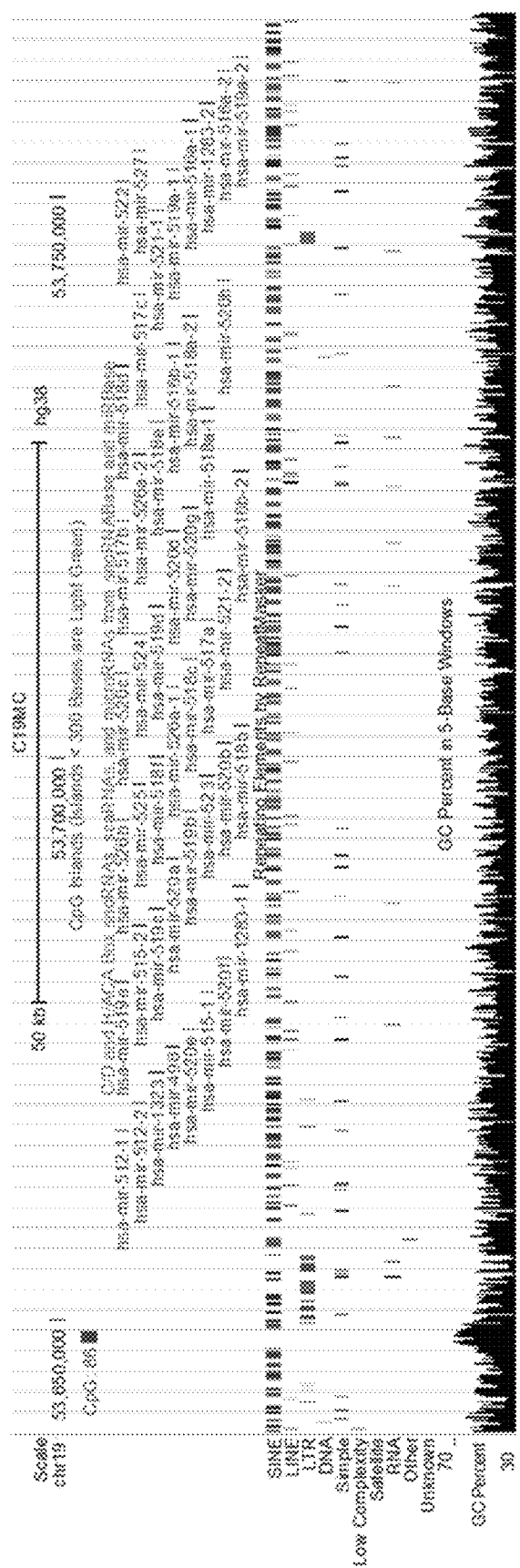

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "sample from a subject" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Disclosed herein are in vitro transcribed (IVT) RNA comprising short interspersed nuclear elements (SINEs). In some embodiments, Alu RNA templates are generated by PCR using primers that have T7 promoter in the forward or reverse strand to allow in vitro transcription of the sense or antisense strands. In vitro transcription of the Alu templates can be carried out using HiScribe T7 High Yield RNA synthesis kit (NEB) with partial of complete nucleotides substitution with modified nucleotides.

Also disclosed herein is a vaccine composition that contains an in vitro transcribed (IVT) RNA comprising short interspersed nuclear elements (SINEs) as disclosed herein, in a pharmaceutically acceptable carrier.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Increase in Alu Transcripts Activates Cellular Defense Response by Inducing Interferon Type III Methods Ethical Approvals Placentas from voluntary terminations of uncomplicated first trimester (7-8 weeks) and early (20 weeks) pregnancies were obtained with written, informed patient consent. This work was carried out with approval from the University of South Florida Institutional Review Board (protocol #00015578). The generation, care, and use of the C19MC humanized mice was carried out at University of Pittsburgh with approval from the Institutional Animal Care and Use Committee[1].

Cell Culture

AD-293 cells (Stratagene 240085), 293T cells (ATCC CRL-3216), NoDice 2-20 cells were a gift from Dr. Bryan Cullen[2] and B16-F10 cells (ATCC CRL-6475) were grown in DMEM supplemented with 10% heat inactivated fetal bovine serum (Millipore-Sigma). HTR8/SVneo (ATCC CRL-3271) cells were cultured in RPMI supplemented with 5% heat inactivated fetal bovine serum. Normal human dermal fibroblasts (NHDF) (Lonza CC-2511) were cultured in Fibrolife Serum-free medium (Lifeline Cell Technology). iPSCs (ATCC ACS-1030) were cultured in Essential 8 medium (ThermoFisher).

For IFNL3 stimulation AD-293 cells were seeded in multi-well plates at a density of $10^5$ cells/mL 24 hours prior to addition of recombinant IFNL3 protein (PBL Assay Science #11730-1) to the medium. After 48 hours, the expression of interferon response genes ISG15 and OAS1 were assessed by RT-PCR.

Transient Activation of C19MC and CYP19A1 Using Cas9-SAM gRNAs were designed to C19MC using the ATUM CRISPR gRNA Design tool to identify PAM sequences near the first miRNA of the cluster. gRNAs for CYP19A1 were designed. Adapter sequences were added to the gRNA prior to oligo synthesis (Oligos #1-8) to allow for Golden Gate cloning into the lenti ssgRNA(MS2)-zeo-backbone (Addgene #61427) and subsequent transformation in to GC10 competent cells. Ampicillin resistant clones were selected and verified by sequencing.

AD-293, 293T, 2-20, or HTR8 cells were seeded in multi-well plates 24 hours before transfection with 1:1:1 mass ratio of ssgRNA(MS2)-zeo, MS2-P65-HSF1 and dCas9-VP64-GFP plasmids (Addgene #61426 and 61422, respectively) using Lipofectamine 2000 (Invitrogen). Cell culture medium was changed after 24 hours.

miRNA and mRNA Sequencing

Total RNA was isolated from HEK293 cells 72 hours after transfection with 759-sgRNA/SAM or 620-sgRNA/SAM using the miRNeasy Kit (QIAGEN) and stored at −80° C. in RNAse-free water.

Two micrograms of total RNA were converted into a small RNA cDNA library as previously described[4]. RNA inputs for each sample were ligated to a barcoded 3' adapter sequence, pooled, size selected, and gel purified before ligation of 5' adapters. The RNA was again size selected and gel purified before second strand synthesis using SuperScript III, alkaline RNA hydrolysis, and 10 cycles of PCR amplification.

Individual RNAseq libraries were quality controlled using an Agilent TapeStation with High Sensitivity D1000 ScreenTape. Indexed samples were quantified using the Qubit dsDNA HS assay and pooled at equimolar concentrations (10 nM). Libraries were sequenced on an Illumina NextSeq 500 using 75-bp paired-end reads in mid-output mode.

Bioinformatics Analysis miRNA sequencing read annotation was performed. Reads that mapped to more than one location were assigned to each mapping transcript as a fraction of the number of mapping locations (fractional mapping). mRNA sequencing reads were aligned to the human genome (GRChg38) using the RNASTAR aligner[6] allowing for two mismatches. Read counts were generated using featureCounts[7] and differential expression analysis was completed using edgeR. Differentially expressed genes were considered significant with an FDR<0.1 and fold-change>2.0 up or down.

ELISA

Enzyme-linked immunosorbance assay for IFNL1/3 (R&D Systems #DY1587) was performed according to the manufacturer's instructions on conditioned cell culture media collected 72 hours after 759-sgRNA/SAM transfection of AD-293, 293T, or 2-20 cells.

In Situ Hybridization

In situ hybridization for hsa-miR-517a/c, as a representative member of the C19MC, and Alu repeats in human and mouse placental sections was performed according to the manufacturer's (Exiqon) instructions. Briefly, paraffin embedded tissue sections were deparaffinized in xylene and rehydrated by a series of graded alcohol washes. In situ hybridization was then performed using 40 nM 5',3'-digoxignein-labeled locked nucleic acids (Exiqon) complementary to has-miR-517a/c (Exiqon #90005), Alu (Oligo #9) or a scrambled control. Hybridization and post-hybridization SSC washes were performed at 55° C. Sections were then blocked, and the hybridization probes were detected using alkaline phosphatase-conjugated sheep anti-digoxignenin Fab fragments (Roche #11093274910). Signal was developed using NBT/BCIP (Roche #11697471001) to produce the dark-blue staining. Nuclei were counterstained using Nuclear Fast Red (Vector Laboratories #H-3403). Slides were then dried and covered for image analysis.

RT-PCR

For mRNA RT-PCR analysis 1 µg total RNA was reverse transcribed using random hexamer or oligo(dT) primers and M-MuLV reverse transcriptase (New England Biolabs #M0253) according to the manufacturers' recommendations. For miRNA cDNA, 0.5 µg total RNA was reverse transcribed using the TaqMan miRNA Reverse Transcription Kit (ThermoFisher Scientific #4366596) according to the manufacturer's instructions.

To assess relative mRNA and miRNA expression levels, RT-PCR of the cDNA products was performed using the following TaqMan RT-PCR probes: human IFNL2/3 (Hs04193048_gH), mouse IFNL2/3 (Mm04204158_gH), OAS1 (Hs00973637_m1), ISG15 (Hs00192713_m1), IFNLR1(Hs00417120_m1), IL10RB (Hs00175123_m1), CYP19A1 (Hs00903411_m1), human GAPDH (Hs02786624_g1), mouse GAPDH (Mm99999915_g1), hsa-miR-515-5p (001112), hsa-miR-516a-5p (002416), hsa-miR-516b (001150), hsa-miR-517a (002402), hsa-miR-518c (002401), hsa-miR-519d (002403), hsa-miR-379 (001138), hsa-miR-412 (001023), hsa-miR-485 (001036), hsa-miR-654 (002239), U18 (001204). TaqMan probes were used according to the manufacturer's instructions with TaqMan Fast Advanced Master Mix (ThermoFisher #4444556) on a QuantStudio 3 (Life Technologies). Expression of mRNA and miRNA was normalized to GAPDH and U18, respectively. Relative expression was calculated using the $2^{-\Delta\Delta Ct}$ method.

Primer Extension

Oligonucleotides complementary to Alu (Oligo #10) and beta actin (Oligo #11) were 5'-labeled with [γ-$^{32}$P]ATP using T4 PNK (New England Biolabs #M0201). The labeled primers were then annealed to 20 µg of total RNA isolated from 293T or 2-20 cells 72 hours after activation of C19MC with sgRNA759/SAM and reverse transcribed with M-MuLV. The resulting DNA was subjected to gel electrophoresis on an 8% TBE-urea gel. The gel was developed on a phosphor storage screen (GE Life Sciences) and scanned using a Amersham Typhoon (GE Life Sciences).

Dot Blotting of dsRNA 1, 2, or 4 µg of total RNA or in vitro transcribed Alu RNA in a 10 µL volume of TE with 350 mM NaCl was loaded onto a wet Biotrace Nitrocellulose membrane (Pall Biosciences) using a Minifold dot-blotter (Schleicher & Schuell, Inc.). The membrane was then baked at 80° C. for 1 hour before blocking for 1 hour at room temperature in Odyssey PBS blocking buffer (LI-COR). The membrane was then probed overnight with J2 mouse anti-dsRNA antibody (Scicons, 1:2000) followed by a 20 minute incubation with IRDye 800CW goat anti-mouse secondary antibody (LI-COR, 1:2500). The membrane was washed three times in TBS-Tween after each antibody incubation. Membranes were imaged on an Odyssey CLx (LI-COR) and analyzed using ImageStudio software (LI-COR).

RNaseA digestion of ssRNA was performed in TE with 350 mM NaCl to block dsRNA digestion. RNaseA was added to the total RNA or in vitro transcribed Alu RNA to a final concentration of 10 µg/mL and incubated for 2 hours at room temperature before dot blotting.

Western Blotting

Protein lysates were fractionated by SDS-PAGE and transferred to Biotrace Nitrocellulose membrane (Pall Biosciences). Membranes were incubated overnight at 4° C. with rabbit anti-alpha tubulin (Cell Signaling Technologies #2144, 1:1000) and rabbit anti-DICER1 (Cell Signaling Technologies #5362S, 1:1000) primary antibodies in Odyssey PBS blocking buffer (LI-COR) before a 20 minute room temperature incubation with IRDye 680 donkey anti-rabbit secondary antibody (LI-COR, 1:5000). Membranes were washed three times in TBS-Tween after each antibody incubation, imaged on an Odyssey CLx (LI-COR), and analyzed using ImageStudio software (LI-COR).

In Vitro Transcription

Template generation using oligos #12-13, in vitro transcription, capping and poly(a) tailing of GFP mRNA was performed. Control 350 nt GFP RNA templates were generated by PCR of pLL3.7 plasmid (a gift from Dr. Luk Parijs, Addgene plasmid #11795) using oligos #14-15. A second round of PCR using oligos #15 and #16 (GFP F) or #14 and #17 (GFP R) was performed to add a T7 promoter for transcription of the sense or antisense strands respectively. Alu RNA templates were similarly generated by PCR of a bacterial artificial chromosome containing C19MC using primer pairs specific for AluJb7 (#18 and #19), AluSz8 (#22 and #23), or AluSx10 (#26 and #27). In addition a template containing all three Alu repeats (Alu3x) was generated using oligos #18 and #27. T7 promoters were added to the 5' end of either strand of the PCR products during a second round of PCR (AluJb7 F: #19 and #20; AluJb7 R: #18 and #21; AluSz8 F: #23 and #24; AluSz8 R: #22 and #25; AluSx10 F:#27 and #28; AluSx10 R: #26 and #29; Alu3x F: #20 and #27; Alu3x R: #18 and #29) to allow transcription of the sense or antisense strands.

In vitro transcription of the GFP and Alu templates was carried out using HiScribe T7 High Yield RNA synthesis kit (NEB) with complete substitution of uridine for pseudouridine (TriLink Biotechnologies, N-1019). The RNA products were precipitated in 5 M ammonium acetate, resuspended in $H_2O$, quantified by spectrophotometry, and stored at $-80°$ C. until use.

Statistics

Two-tailed Student's T-test or one-way ANOVA with Tukey's post-hoc test were used when appropriate for testing statistical significance using GraphPad Prism 7 software. P<0.05 was considered to be statistically significant unless specified differently in the relevant figure legend. All data are representative of at least three independent experiments unless otherwise noted in the relevant figure legends.

Results and Discussion

Transcriptional Activation of 100 kb C19MC Cistron by CRISPR/SAM

To investigate the role of Alus in physiological settings, focus was on the largest human microRNA (miRNA) cistron, mir-498(46) cistron located on chromosome 19, known as C19MC. This miRNA cluster spans over 100 kb and contains 46 miRNA genes and 265 Alus are embedded in both the sense and antisense strand. C19MC is epigenetically regulated by imprinting. In the placenta, the paternal allele is transcribed by polymerase II as a single RNA transcript (FIG. 1A) (Noguer-Dance, M. et al., Human molecular genetics 19:3566-3582 (2010)). To transcriptionally activate the entire C19MC cistron, the CRISPR/Cas9-SAM (SAM) technology (Konermann, S. et al., Nature 517:583-588 (2015)) was employed using two different single guide RNA (sgRNAs), the 620-sgRNA which binds at ~579 bp upstream of the first miRNA or the 759-sgRNA that binds at ~171 bp upstream of the first two miRNAs of the cistron. Small RNA sequencing (sRNAseq) analysis of AdHEK cells transiently transfected with 759-sgRNA/SAM, 620-sgRNA/SAM or GFP control for 72 hours showed a consistent increase, up to 8,000-fold, in the expression of 39 miRNAs of the C19MC cistron (threshold: >2-fold, FDR 0.10) (FIG. 1B). Five other miRNAs were upregulated in both 759- and with 620-sgRNA/SAM transfected cells, however none of them belonged to the C19MC cistron (FIG. 1B). On the other hand, only 3 miRNAs were consistently downregulated by 759- and 620-sgRNA/SAM, but none of them belonged to the C19MC cistron (FIG. 1O). The 8 differentially expressed miRNAs (3 downregulated and 5 upregulated) in both 759- or 620-sgRNA/SAM-transfected cells may be regulated by the C19MC. Activation of C19MC was confirmed by RT-PCR, demonstrating a 135-fold increase in miR-517a, a member of C19MC, after 759-sgRNA/SAM transfection compared to GFP control. These data show that CRISPR/SAM technology specifically activate the C19MC cistron with minimal off target effects.

C19MC Induces Interferon and Cellular Defense Response

To gain insight into the possible regulatory pathways affected by the C19MC cistron, RNAseq was performed followed by gene set enrichment analysis of the 757 genes that were differentially expressed in both 759-sgRNA/SAM and 620-sgRNA/SAM compared to control GFP transfected cells (FDR≤0.10, <−2 and >2-fold), demonstrating that cellular defense, cytokines, interferon and innate immune response to be the most enriched (FIG. 1D). Interferons (IFNs) are known for their potent antiviral and immunomodulatory activities. Type I IFNs includes 13 IFN-α (IFNAs) subtypes and a single IFN-β (IFNB1) subtype, which can be induced and secreted from most cell types. They signal through the heterodimeric receptor complex (IFNAR1/2), found in all nucleated cells that activate hundreds of downstream IFN-stimulated genes (ISGs) resulting in a potent systemic antiviral state. On the other hand, type II IFNs consist of only IFN-γ (IFNG), which is induced and secreted predominantly by activated T cells, natural killer (NK) cells, B cells and antigen-presenting cells (APCs). IFN-γ signals through the IFNγRα and IFNγRβ subunits found on most cell types. Type III IFNs includes IFN-λ1 (INFL1), IFN-λ2 (IFNL2), IFN-λ3 (IFNL3) and IFN-λ4 (IFNL4), although the last is found only in a subset of human population due to a single-nucleotide polymorphism correcting a frameshift mutation in a pseudogene (Prokunina-Olsson, L. et al., Nat Genet 45:164-171 (2013)). Type III IFNs signal through a distinct receptor complex, IFNλR1 and IL10-R2 subunits, found mostly in cells of epithelial origin to activate hundreds of downstream ISGs, similar to type I IFN signaling. Both type I and III IFNs are key cytokines produced during innate immune response upon activation of pattern-recognition receptors (PRRs) by pathogens including viral, microbial, fungal and parasite infections (Uematsu, S. et al. J Mol Med (Berl) 84:712-725 (2006); Syedbasha, M. et al., Front Immunol 8:119 (2017)). However, type I IFNs control infection systemically whereas type III IFNs are locally induced to control infection at barrier surfaces (Wells, A. I. et al., Trends Immunol 39:848-858 (2018)). Importantly, human trophoblasts cells constitutively release type III IFNs, even in the absence of viral infection, and the molecular mechanism that trigger the constitutive expression of IFNs is still unknown (Wells, A. I. et al., Trends Immunol 39:848-858 (2018); Ander, S. E. et al., Sci Immunol 4 (2019)).

RNAseq analysis show that transcriptional activation of C19MC cistron highly induced IFNL2 (419.8- and 76-fold in 759- and 620-sgRNA/SAM, respectively), IFNL3 (515- and 104-fold in 759- and 620-sgRNA/SAM, respectively) and numerous IFN-response genes including OAS1. The increase in miR-517a, a member of the C19MC, IFNL2 and IFNL3 expression in AdHEK cells transfected with 579-sgRNA/SAM were confirmed by RT-PCR using Taqman probes that recognizes both mRNAs due to their >96% sequence homology (FIGS. 1E and 1F). the expression level of IFNL receptor complex subunits, IFNLR1 and IL10-RB in AdHEK293 were also measured with or without 759-sgRNA CRISPR/SAM, demonstrating comparable CT values of both FNLR1 and IL10-RB (FIG. 1G). Moreover, when increasing amounts (0-4000 µg/mL) of recombinant IFNL1/3 was added to AdHEK293 cells media resulted in a dose dependent increase in interferon response genes OAS1 and SG15 in manner (FIG. 1H). To further confirm the relationship between C19MC cistron and IFNL2 and IFNL3, the endogenous C19MC cistron was transcriptionally activated using 759-sgRNA/SAM in human trophoblast cell line, HTR-8/SVneo cells, that does not express the C19MC cistron and found 1600-fold (FIG. 1I) and 99-fold (FIG. 1J) increase in miR-517a and IFNL2/3 expression, respectively. The same effects were also found in MCF-7 cells transfected with 759-sgRNA/SAM increased the expression of C19MC and IFNL2/3 expression (FIGS. 1K and 1L). These data confirm that transcriptional activation of the C19MC cistron induces IFNL2/3 expression and its downstream antiviral response genes in different cell types, even in the absence of any viral infections.

C19MC Induces IFN Response in a microRNA Independent Mechanism

Figures 2A, 2B:
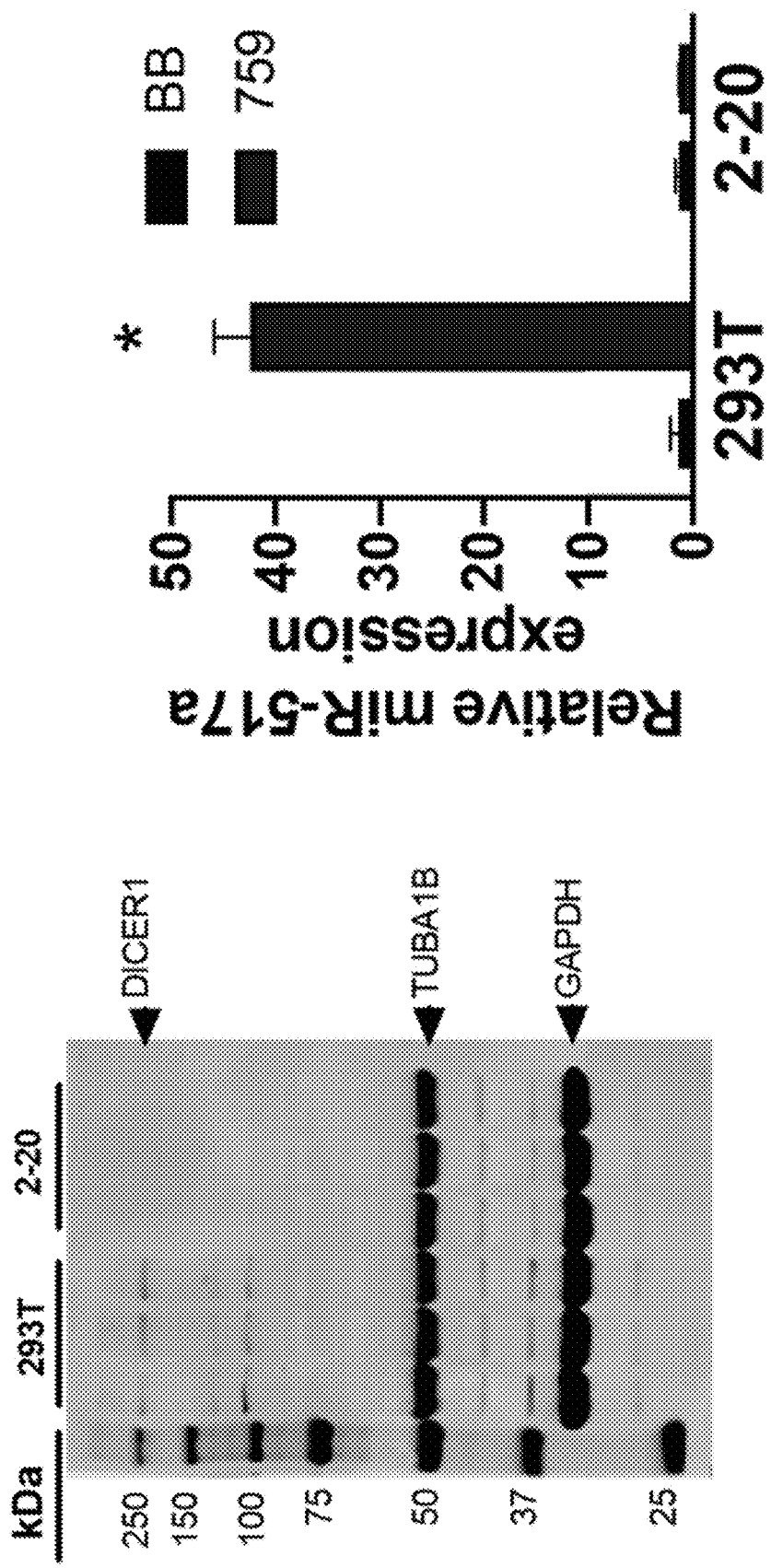
FIGS. 2A to 2D. Induction of IFNL2/3 by transcriptional activation of C19MC is independent of miRNA activity.
Figure 2D:
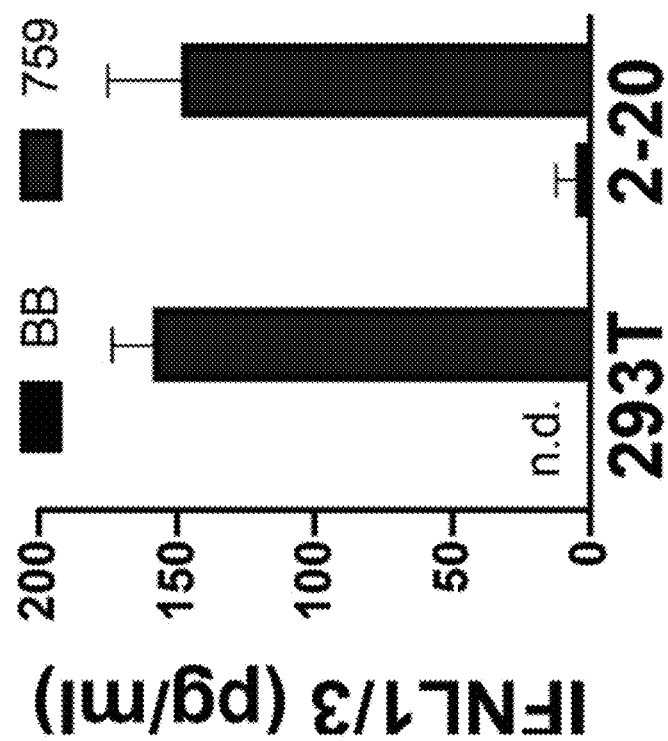
Figure 2C:
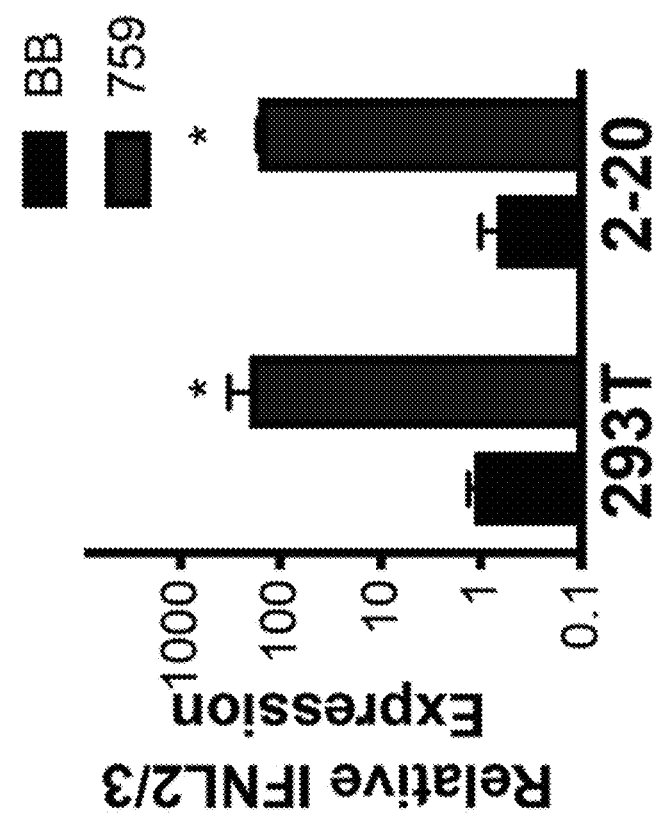

To determine whether the increase in IFNL2/3 and the cellular defense in response to activation of the C19MC cistron is due to the increase in the miRNAs of the C19MC cistron, 759-sgRNA/SAM-mediated upregulation of C19MC was performed in DICER1 knockout HEK293T cells (NoDice 2-20, FIG. 2A) (Bogerd, H. P. et al., RNA 20:923-937 (2014)), followed by RT-PCR for miR-517a and IFNL2/3 where backbone sgRNA (BB-sgRNA) was used as control. As expected, miR-517a was >40 fold induced in 759-sgRNA/SAM transfected HEK293T cells but not in NoDice 2-20 cells (FIG. 2B). Importantly, the expression levels of IFNL2/3 in NoDice 2-20 cells transfected with 759-sgRNA/SAM were >100-fold compared to BB-gRNA/Sam transfected cells, very similar to 759-sgRNA/SAM transfected HEK293T cells (FIG. 2C). Moreover, the levels of IFNL3 in the supernatant of NoDice 2-20 cells transfected with 759-sgRNA/SAM were 2120 µg/ml, similar to the HEK293T cells transfected with 759-sgRNA/SAM (FIG. 2D). Importantly, the accumulation of pre-miRNA in NoDice 2-20 cells did not induce INFL2/3 when cells were transfected with 759-sgRNA/SAM or BB-sgRNA/SAM (FIGS. 2B and 10). RNAseq was also performed, identifying genes that are involved in interferon type III and cellular defense to be the induced in 759-sgRNA/SAM compared to BB-sgRNA/SAM transfected cells. These data demonstrate that the increase in the defense and in IFN response after 759-sgRNA/SAM transfection is independent of the mature miRNA and suggest that other RNA transcripts present in the C19MC, such as the repetitive Alu elements may be responsible for the induction of IFNL2/3 and the defense response.

C19MC Induce IFN Response by Increasing Alu RNA

Figure 3A:
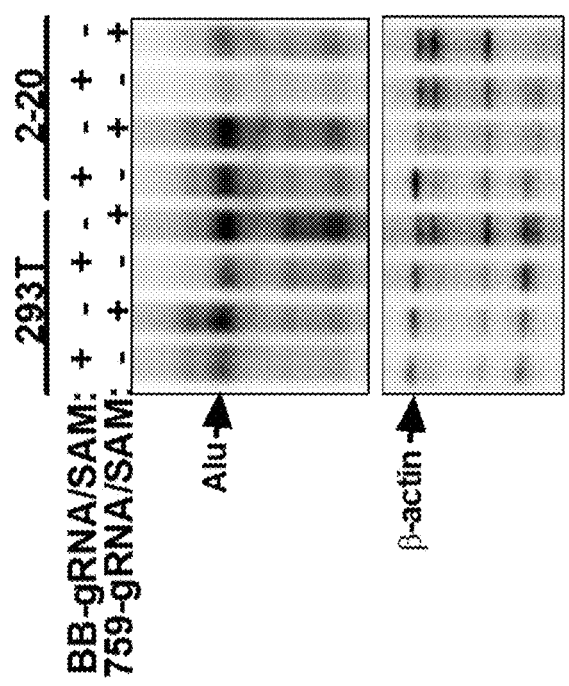
FIGS. 3A to 3F. IFNL2/3 expression after C19MC activation is driven by Alu RNA production.

To test whether transcriptional activation of the C19MC cistron increases the expression of the embedded Alu repeats, primer extension was performed using an Alu probe, demonstrating increase in the Alu RNA abundance in both HEK293T and NoDice 2-20 cells transiently transfected with 759-sgRNA/SAM compared to BB-sgRNA/SAM (FIG. 3A).

Figure 3B:
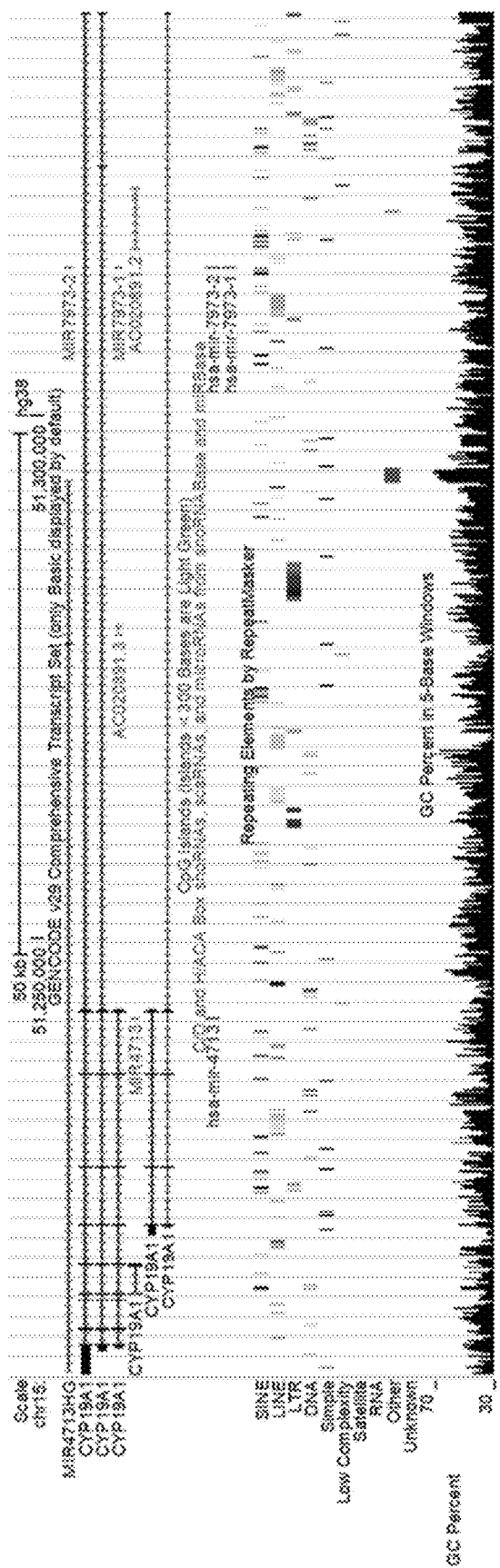
Figure 3C:
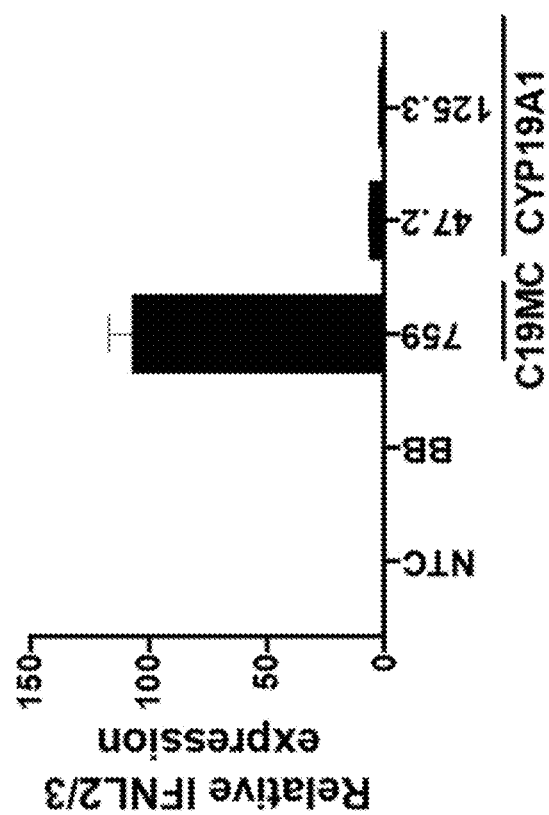
Figure 3D:
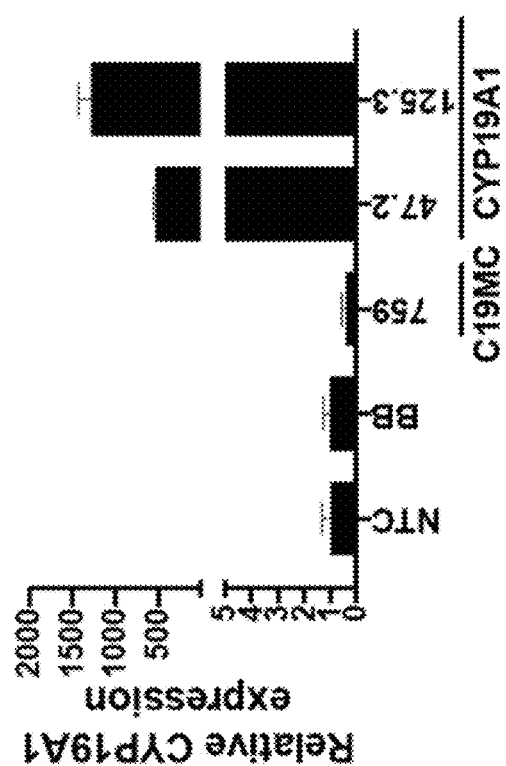

To test whether the increase in IFNL2/3 is due to increase in the transcription of the Alu elements that are located in the C19MC cistron, the CRISPR/Cas9-SAM technique was used to transcriptionally activate another large gene CYP19A1, which span over ~130 kb and is highly expressed in syncytiotrophoblast similar to C19MC, but contains only 23 Alu elements (FIG. 3B). Two sgRNAs (47.2- and 125.3-sgRNA) were designed that bind around the 150 bp upstream of the transcription start site. HEK293T cells transfected with 47.2-sgRNA/SAM or 125.3-sgRNA/SAM increased >500-fold CYP19A1 the expression but did not induce IFNL2/3 expression, whereas cells transfected with 759-sgRNA/SAM that activated C19MC resulted in >100-fold increase in IFNL2/3 (FIGS. 3C and 3D). These data confirm that the increased transcription of the repetitive elements may be responsible for the induction in interferon response.

Figure 3E:
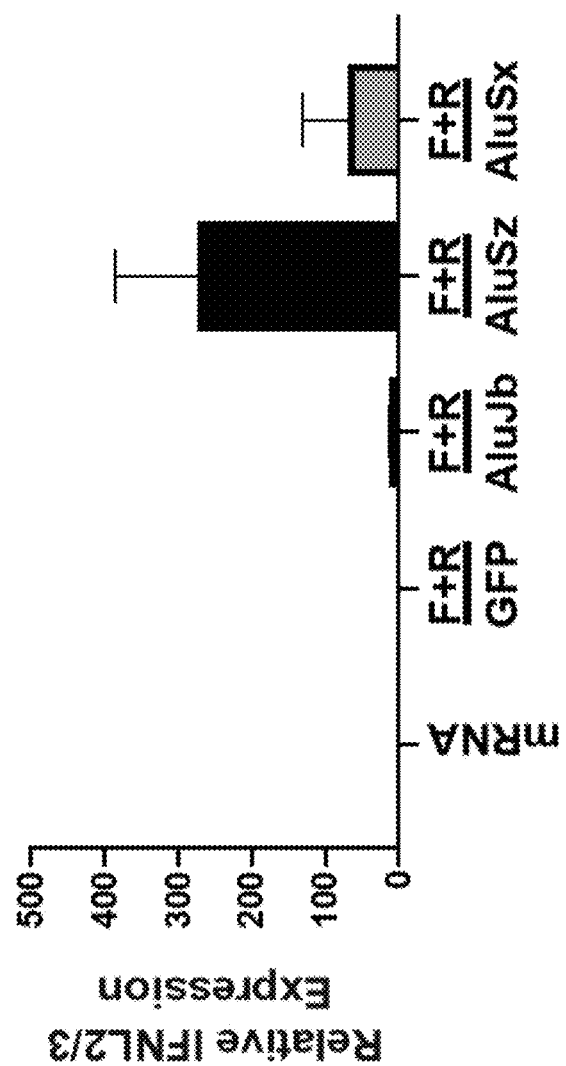
Figure 3F:
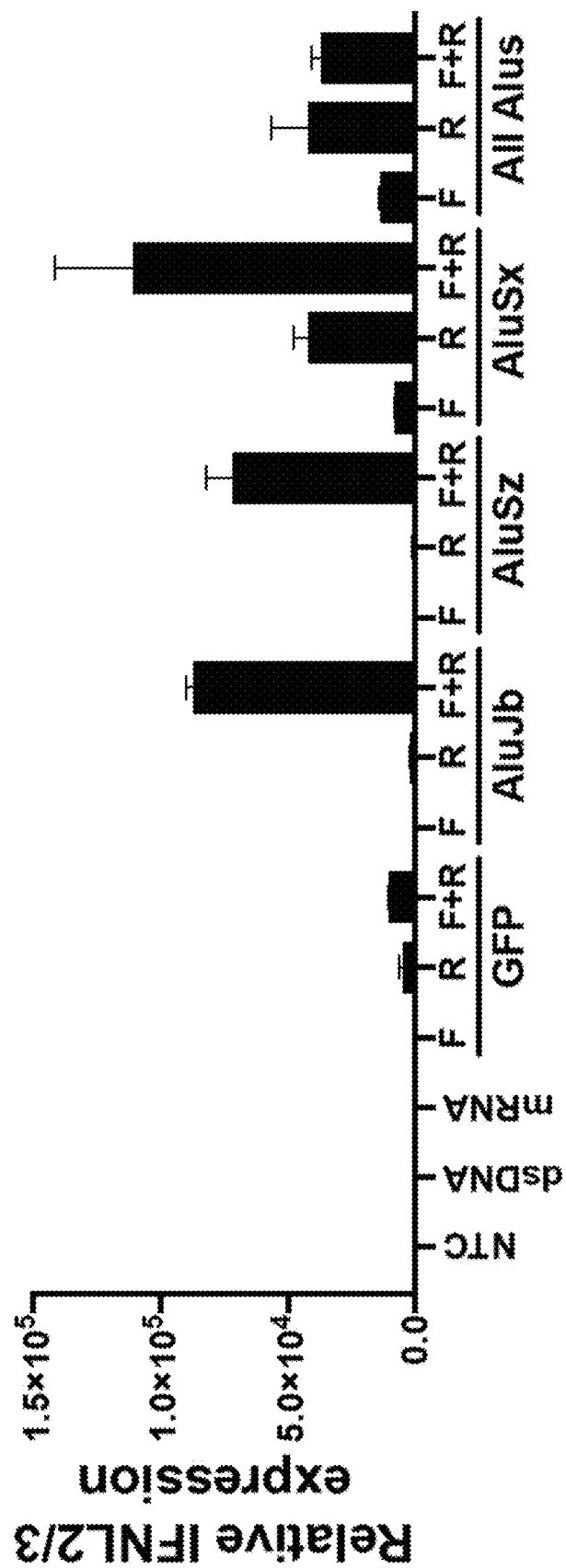

To directly test the effect of Alu RNA on IFNL2/3 expression, and since the C19MC cistron contains Alu repeats in both sense and antisense directions, AluJb-, AluSx-, or AluSz-RNA were in vitro transcribed in both the forward and reverse direction with 100% pseudouridine substitution to reduce the innate immune response to unmodified RNA (Kariko, K. et al., Mol Ther 16:1833-1840 (2008)). HEK293T or HTR8/SVneo cells transfected with the sense and antisense AluJb, AluSx or AluSz RNA resulted in increased IFNL2/3 expression compared to cells transfected with a control dsDNA, GFP mRNA capped and poly(A)-tailed or a 300 base GFP RNA fragment transcribed in the sense and antisense (FIGS. 3E and 3F). These results further confirm that increased expression of the sense and antisense Alu RNA induce IFN type III in the absence of viral infection.

Figures 4A, 4B:
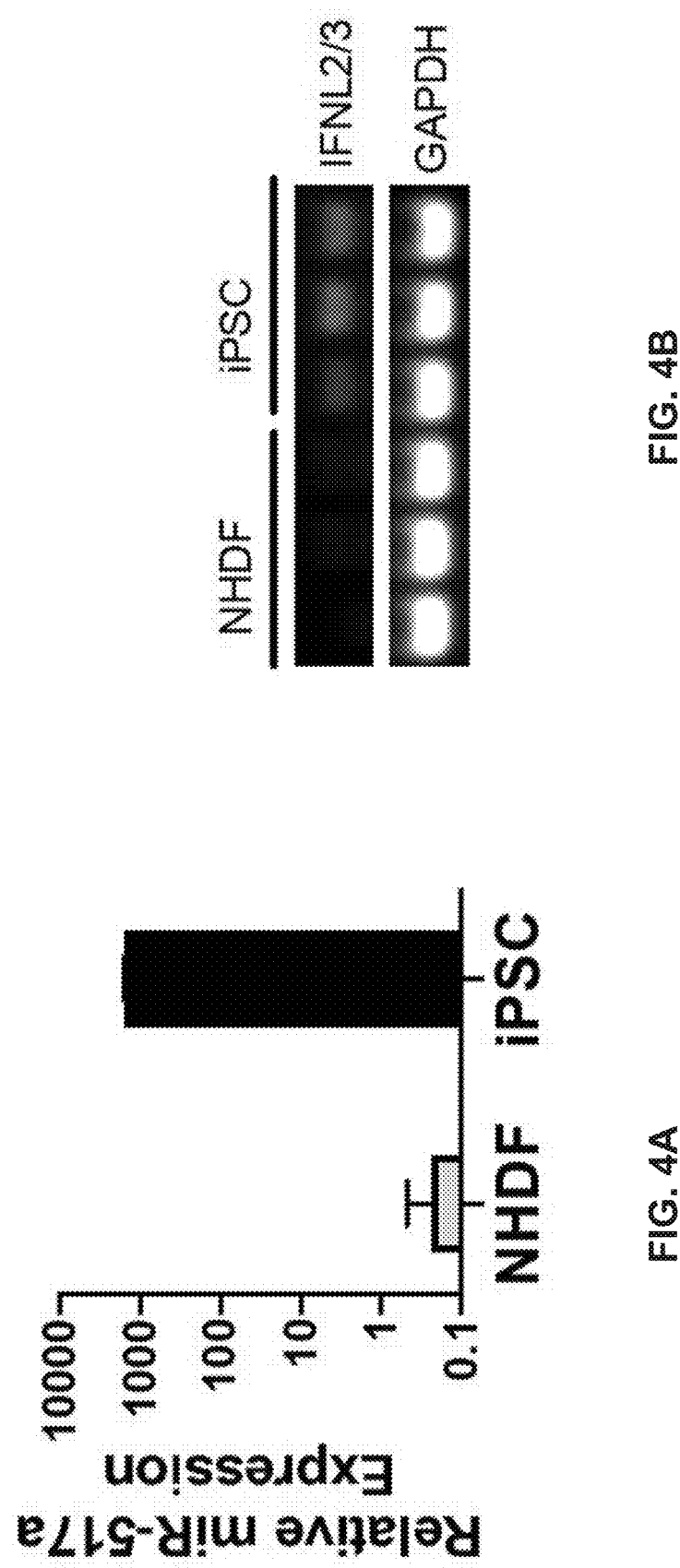
FIGS. 4A to 4E. Colocalization of C19MC and Alu RNA in human and C19MC-transgenic mouse placentas (FIGS. 4A-4B) RT-PCT of hsa-miR-517a normalized to U18 (FIG. 4A) or representative agarose gel of IFNL2/3 and GAPDH (FIG. 4B) in iPSC and differentiated normal human fibroblast (NHDF).
Figure 4C:
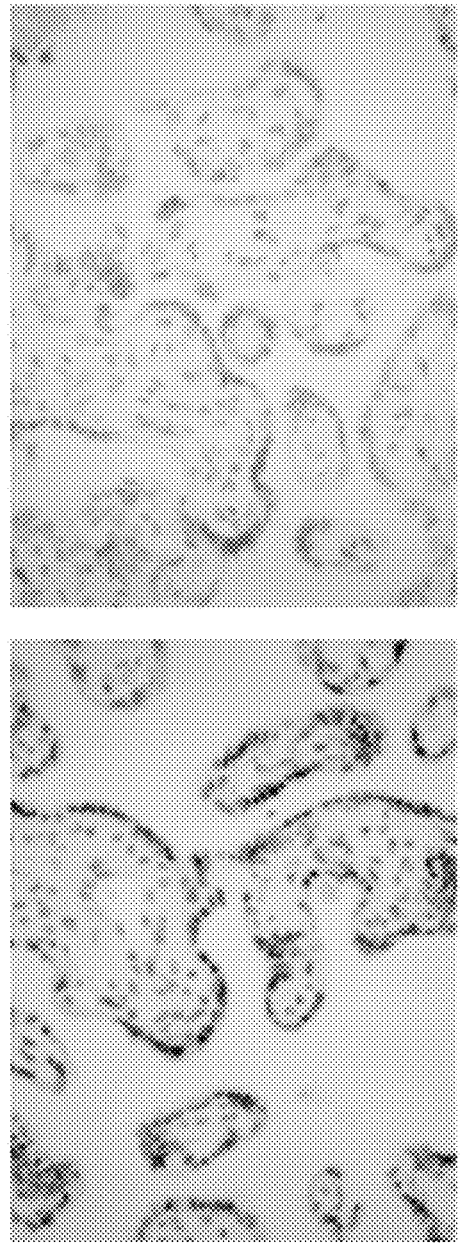
Figure 4D:
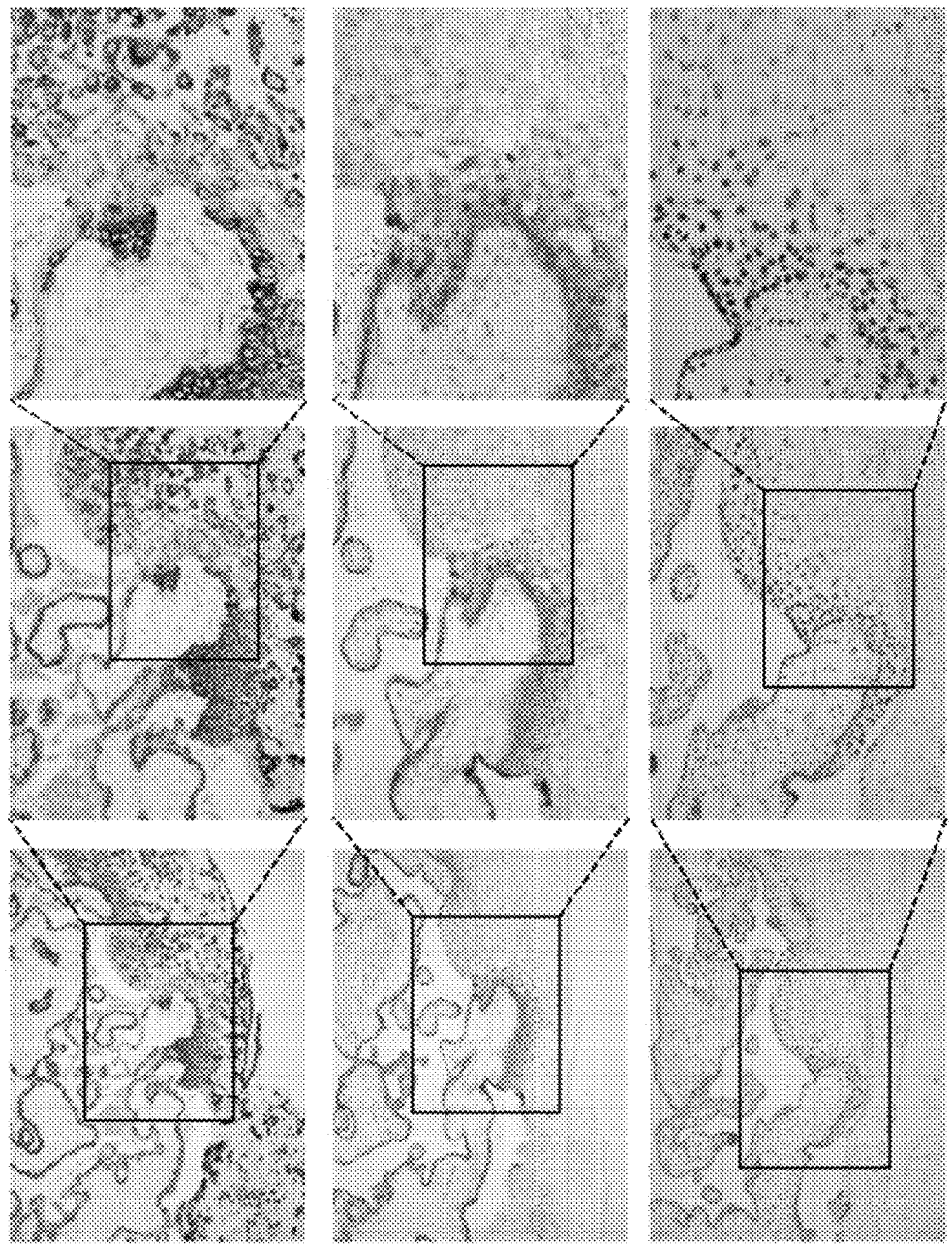
Figure 4E:
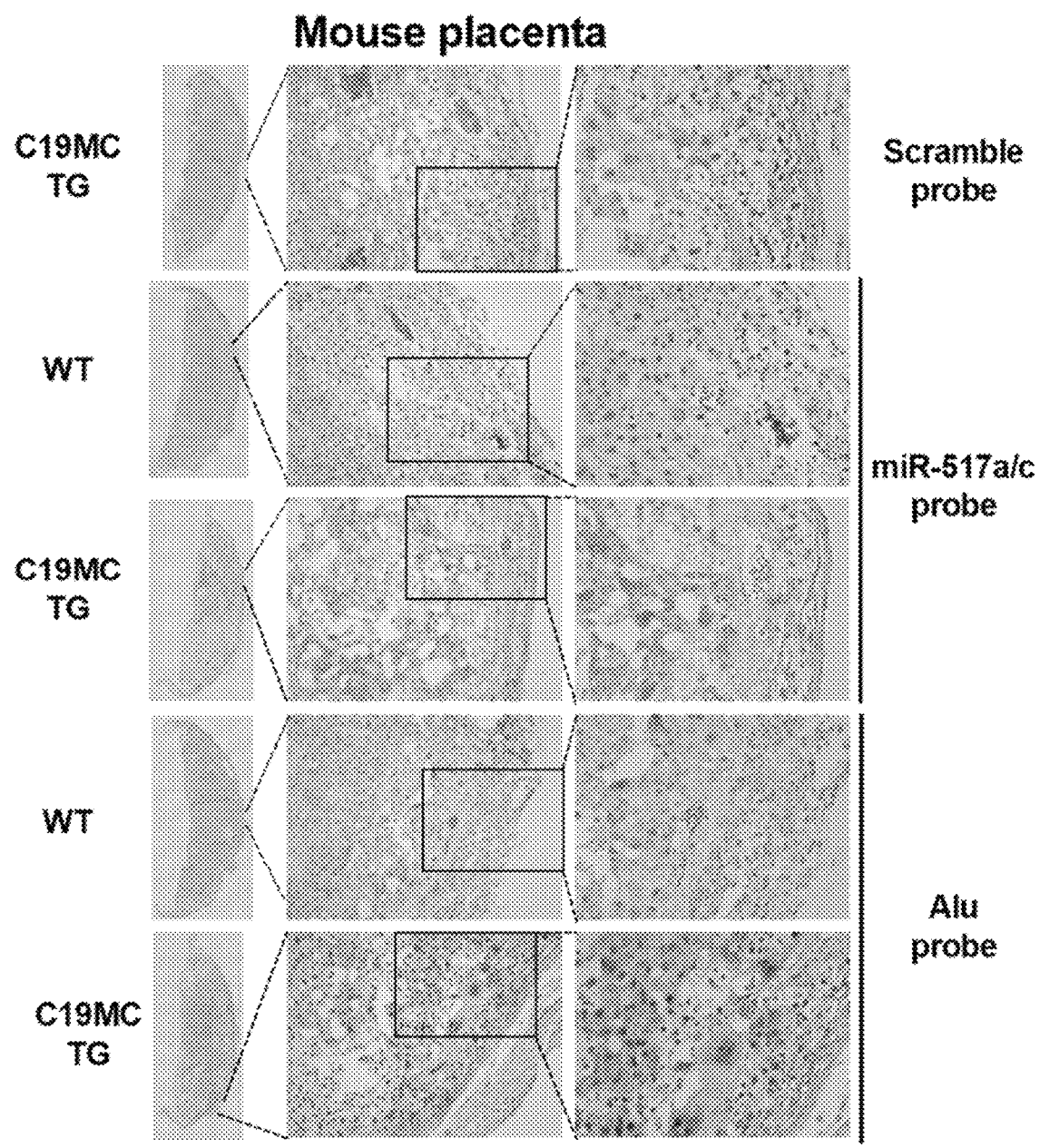

C19MC-Mediated Alu RNA Expression Causes Constitutive/FN Response in Pluripotent Stem Cells and in the Placenta In addition to the high level of expression in the placenta, C19MC is also strongly expressed in pluripotent stem cells. The expression of IFNL2/3 was examined in iPSCs de-differentiated from human blood (Churko, J. M. et al., Methods Mol Biol 1036:81-88 (2013)), demonstrating high expression of both C19MC miRNA as represented in miR-517a (FIG. 4A) and IFNL2/3 compared to differentiated normal human fibroblast (FIG. 4B). C19MC cistron is known to be highly expressed in the villus trophoblasts and is lost as they differentiate into extravillus trophoblast. To test whether the expression of C19MC also produce Alu RNA transcripts in situ, in situ hybridization was performed using probes designed to recognize Alu transcripts on paraffin embedded term placental sections pretreated with or without RNaseA. Strong expression of Alu RNA was found in the villus trophoblasts which was abolished by RNaseA treatment (FIG. 4C). These data confirm that the Alu probe recognizes Alu RNA transcripts and not the genomic Alus. To further confirm the co-localization of the Alu transcripts with the C19MC cistron, in situ hybridization was performed using miR-517a/c- or the Alu probe (a member of the C19MC cistron) on adjacent consecutively cut paraffin embedded placental sections from first trimester and early pregnancies. Immunohistochemical staining for cytokeratin and vimentin were also performed to distinguish between trophoblasts and decidual cells, respectively. Similar to miR-517a/c, Alus were highly expressed in the villus trophoblasts and proliferative trophoblastic cell columns in anchoring villi and gradually decreased as the trophoblast differentiated and invaded the decidua (FIG. 4D). Since Alu repeats and C19MC cistron are specific to primates, in situ hybridization was performed with miR-517a/c or Alu probe on paraffin embedded placental sections from VVT or C19MC transgenic mice (Chang, G. et al., FASEB J 31:2760-2770 (2017)), demonstrating that miR-517a/c and Alus were highly expressed in the fetal labyrinth and the junctional zone, while the maternal decidual area was negative (FIG. 4C). Taken together, these data demonstrate that primates have developed a specific exaptation by which constitutive expression of C19MC Alu RNA in pluripotent stem cells and in the placental villus trophoblasts to induce IFNL2/3 and the cellular defense response to protect the developing fetus before the immune system is fully developed.

Increase in Alu RNA Induce IFNL Response in Somatic Cells

Figure 5:
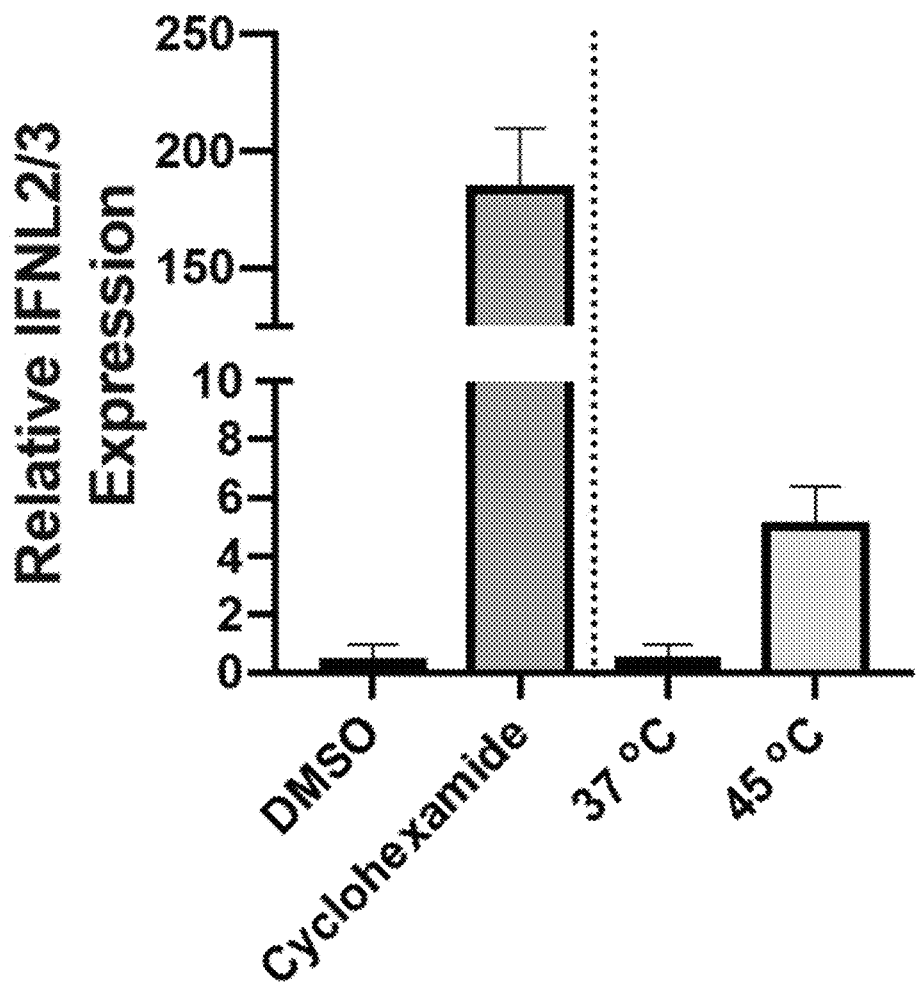
FIG. 5. Induction of Alu expression by cellular stress activates IFNL2/3 expression. RT-PCR for IFNL2/3 normalized to GAPDH in HeLa cells treated with 100 μg/ml cyclohexamide for 4 hr, or heat shock for 30 min at 45° C. and allowed to recover for 2 hr prior to collection of total RNA.

Alus repeats are the most abundant transposable elements in the human genome and can be independently transcribed by RNA polymerase III in response to various stress conditions. Previous studies have shown that viral infection increases Alu transcription (Chu, W. M. et al., Mol Cell Biol 18:58-68 (1998)), while others showed that viral infection induces IFNL2/3 expression and interferon response (Kotenko, S. V. et al., Nat Immunol 4:69-77 (2003)). It is established that cellular treatment with cycloheximide or heat shock also increase Alu transcription (Chu, W. M. et al., Mol Cell Biol 18:58-68 (1998)). However, the effect of these treatments on IFNL2/3 expression was not tested. Here we show that HeLa cells treated with cycloheximide or subjected to heat shock also increased IFNL2/3 expression (FIG. 5A). This concomitant increase in Alu and IFNL2/3 expression indicates that Alus may also have been adapted to prime the innate immune response in somatic cells and bolster anti-viral defenses during cellular stress.

Once considered "junk" DNA or even "parasitic" genes, Alu repeats have been found to have functional roles in regulation of gene expression during transcription, RNA editing and translation (Hasler, J. et al., Nucleic Acids Res 34:5491-5497 (2006)). Disclosed herein is a new role of the Alu repeats in activating type Ill interferon during cellular stress to heighten the anti-viral state. Furthermore, the expression of the Alu-rich C19MC cistron in pluripotent stem cells and placental trophoblasts drives the constitutive expression of type III interferon and creates a formidable anti-viral barrier to the developing fetus.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A vaccine, comprising in vitro transcribed (IVT) RNA comprising short interspersed nuclear elements (SINEs) and an antigen in a pharmaceutically acceptable carrier, wherein the IVT RNA comprises pseudouridine and no uridine.

2. The vaccine of claim 1, wherein the SINE comprises Alu repeats.

3. The vaccine of claim 1, wherein the SINE comprises AluJ, AluS, and/or AluY RNA sense strands, antisense strands, or a combination thereof.

4. A composition comprising: in vitro transcribed (IVT) RNA comprising short interspersed nuclear elements (SINEs), wherein the IVT RNA comprises pseudouridine and no uridine.

5. The composition of claim 4, wherein the SINE comprises Alu repeats.

6. The composition of claim 4, wherein the SINE comprises AluJ, AluS, or AluY RNA sense strands, antisense strands, or a combination thereof.

7. The composition of claim 4, wherein the IVT RNA comprises a combination of AluJ, AluS, and AluY RNA sense strands and antisense strands.

8. A pharmaceutical composition comprising: in vitro transcribed (IVT) RNA comprising short interspersed nuclear elements (SINEs) and a pharmaceutically acceptable carrier, wherein the IVT RNA comprises pseudouridine and no uridine.

9. The pharmaceutical composition of claim 8, wherein the SINE comprises Alu repeats.

10. The pharmaceutical composition of claim 8, wherein the SINE comprises AluJ, AluS, or AluY RNA sense strands, antisense strands, or a combination thereof.

11. The pharmaceutical composition of claim 8, wherein the IVT RNA comprises a combination of AluJ, AluS, and AluY RNA sense strands and antisense strands.

* * * * *

UNITED STATES PATENT AND TRADEMARK OFFICE
CERTIFICATE OF CORRECTION

| | | |
|---|---|---|
| PATENT NO. | : 11,844,809 B2 | |
| APPLICATION NO. | : 17/834611 | |
| DATED | : December 19, 2023 | |
| INVENTOR(S) | : Hana Totary-Jain | |

It is certified that error appears in the above-identified patent and that said Letters Patent is hereby corrected as shown below:

In the Specification

Column 1, Line 19, "Alu/restriction" should be --*AluI* restriction--.

Column 2, Line 48, "NJ")" should be --"Ψ"--.

Column 3, Line 3, "10" should be --1C--.

Figure 1C:
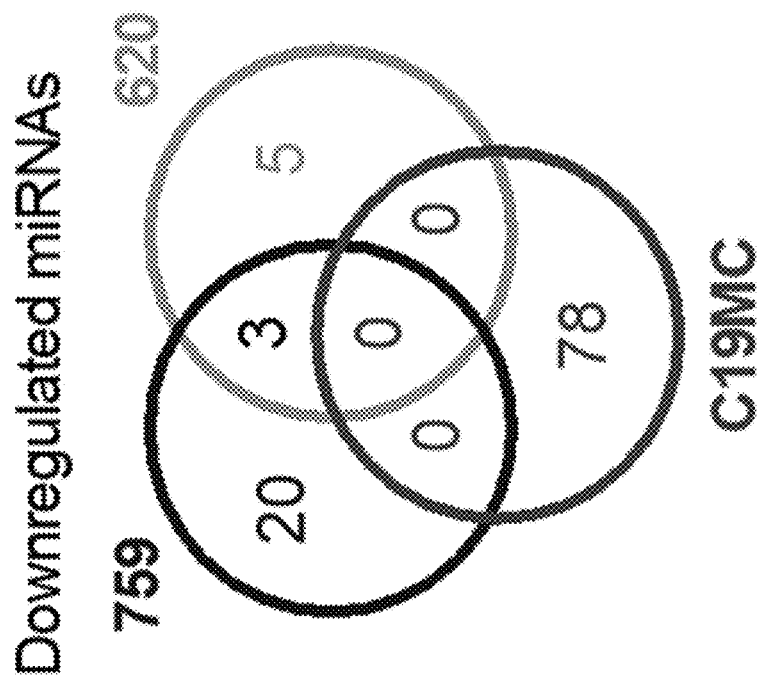
Figure 1B:
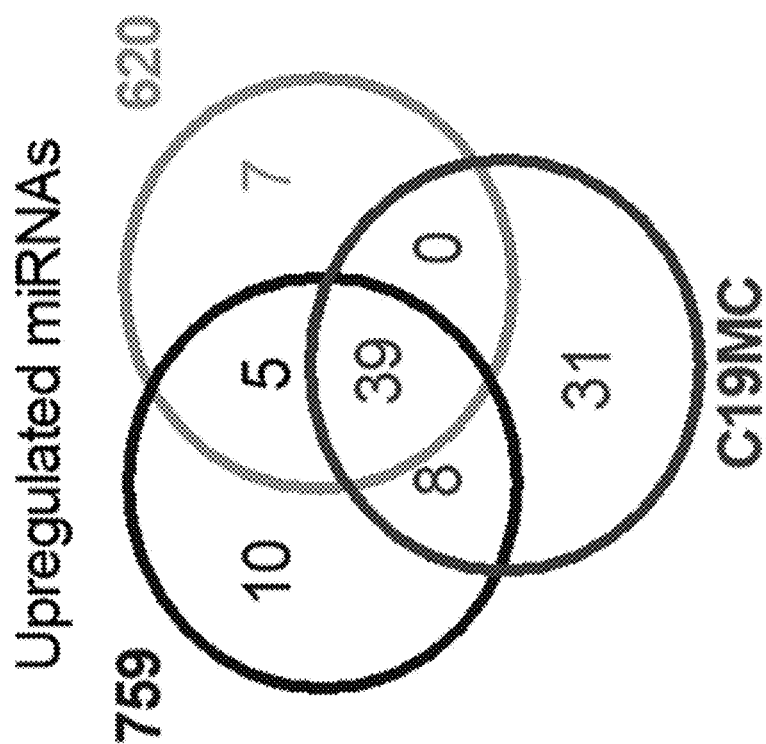
Figures 1E, 1F:
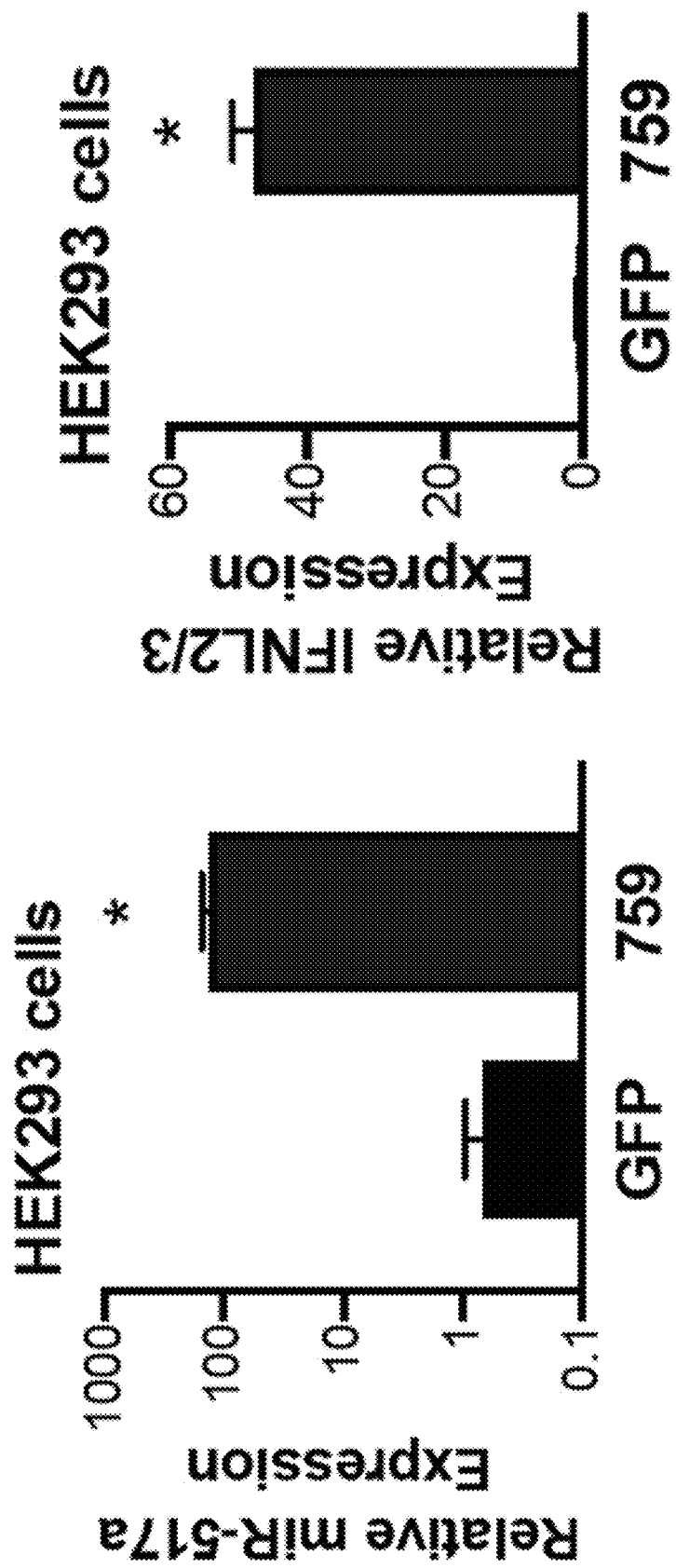
Figure 1H:
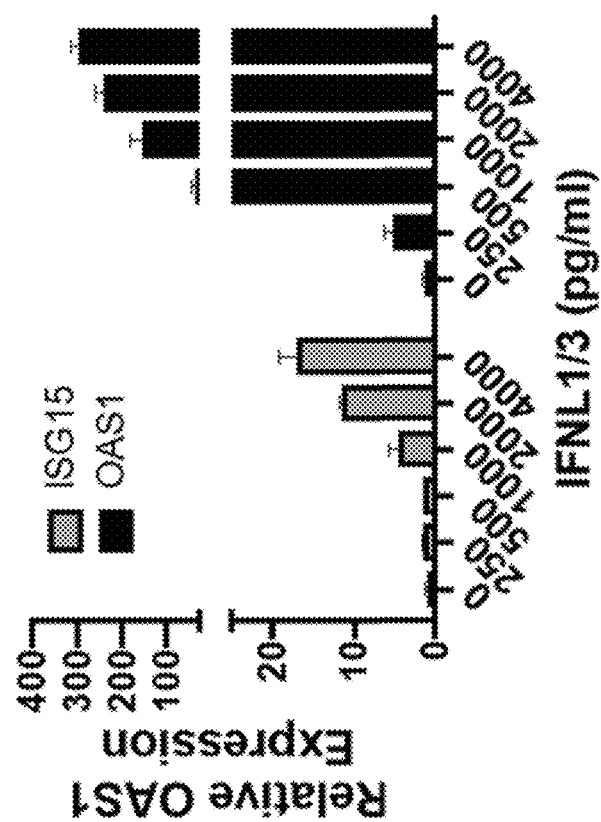
Figure 1G:
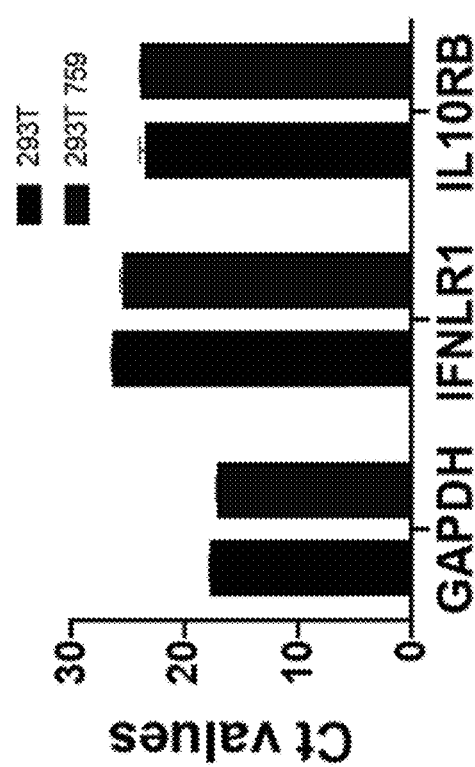
Figure 1J:
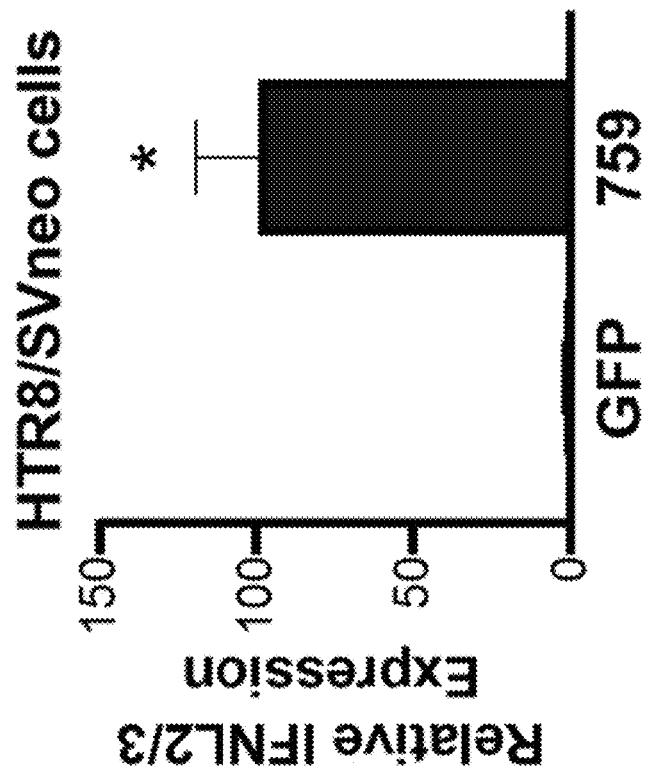
Figure 1I:
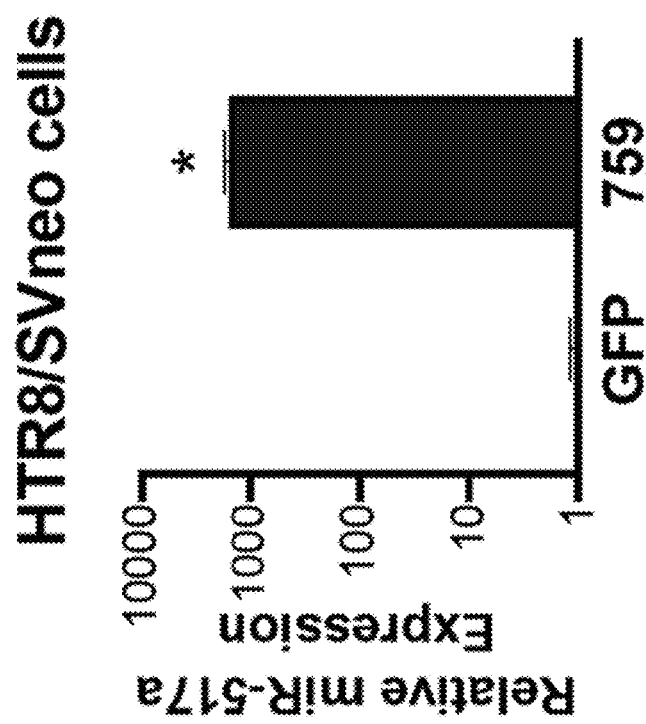
Figure 1L:
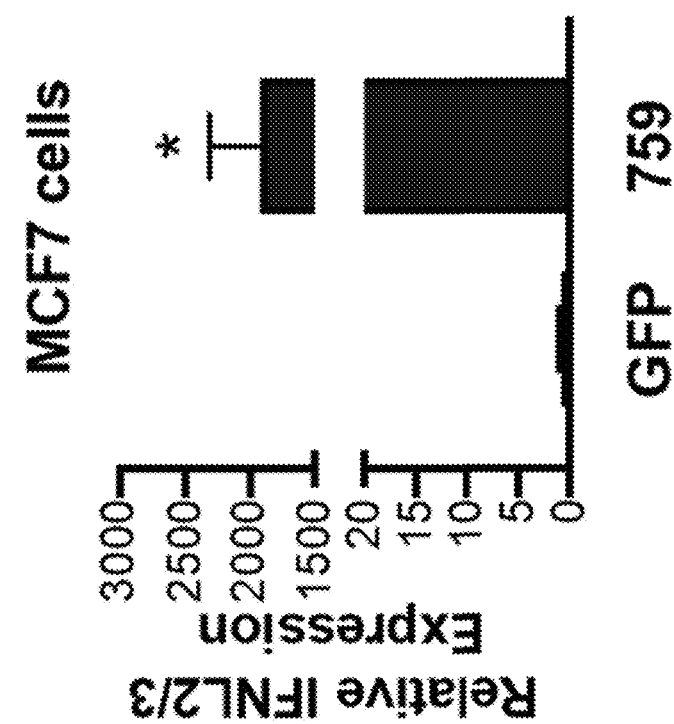
Figure 1K:
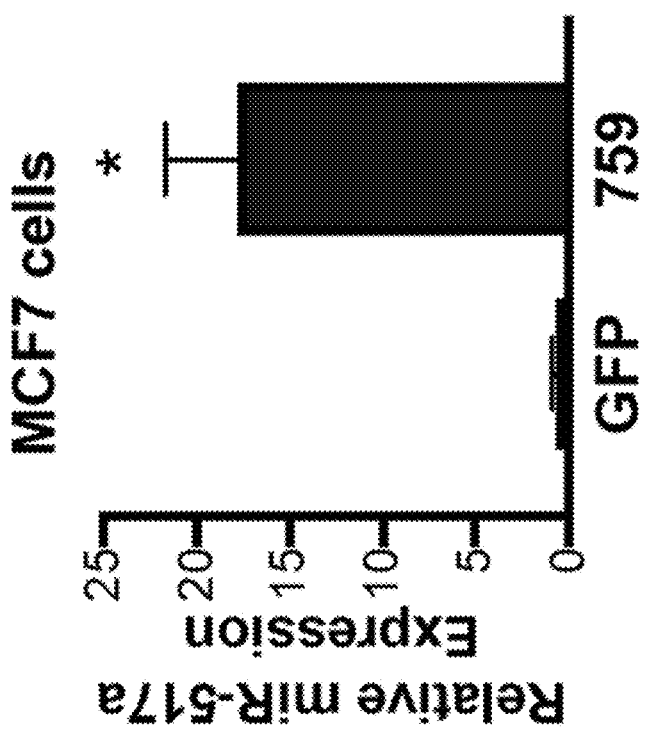

Column 3, Line 4, "FIG. 10" should be --FIG. 1C--.

Column 3, Line 67, "VVT" should be --WT--.

Column 9, Line 66, "FIG. 10" should be --FIG. 1C--.

Column 11, Line 1, "µg/mL" should be --pg/mL--.

Column 11, Line 36, "µg/ml" should be --pg/ml--.

Column 11, Line 41, "10" should be --1C--.

Column 12, Lines 25-26, "Constitutive/FN" should be --constitutive IFN--.

Column 12, Line 60, "VVT" should be --WT--.

Signed and Sealed this
Fifth Day of March, 2024

Katherine Kelly Vidal
*Director of the United States Patent and Trademark Office*